United States Patent
Mande et al.

(10) Patent No.: US 9,008,974 B2
(45) Date of Patent: Apr. 14, 2015

(54) TAXONOMIC CLASSIFICATION SYSTEM

(75) Inventors: Sharmila Shekhar Mande, Hyderabad (IN); Maheedhar Reddy Rachamalla, Hyderabad (IN); Monzoorul Haque Mohammed, Hyderabad (IN)

(73) Assignee: Tata Consultancy Services Limited (IN)

( * ) Notice: Subject to any disclaimer, the term of this patent is extended or adjusted under 35 U.S.C. 154(b) by 585 days.

(21) Appl. No.: 13/337,382

(22) Filed: Dec. 27, 2011

(65) Prior Publication Data

US 2012/0278362 A1 Nov. 1, 2012

(30) Foreign Application Priority Data

Apr. 30, 2011 (IN) .......................... 1363/MUM/2011

(51) Int. Cl.
G06F 19/14 (2011.01)
G06K 9/62 (2006.01)
G06F 19/24 (2011.01)

(52) U.S. Cl.
CPC .............. G06F 19/14 (2013.01); G06K 9/6276 (2013.01); *G06F 19/24* (2013.01)

(58) Field of Classification Search
CPC .................................. G06F 19/14; G06F 19/22
See application file for complete search history.

(56) References Cited

U.S. PATENT DOCUMENTS

| | | | | |
|---|---|---|---|---|
| 6,263,334 | B1 * | 7/2001 | Fayyad et al. ................. | 707/737 |
| 8,363,961 | B1 * | 1/2013 | Avidan et al. ................. | 382/225 |
| 2002/0147703 | A1 * | 10/2002 | Yu et al. ............................ | 707/2 |
| 2006/0259249 | A1 * | 11/2006 | Sampath et al. ................. | 702/20 |
| 2007/0059728 | A1 * | 3/2007 | Malanoski et al. .............. | 435/6 |
| 2008/0195612 | A1 * | 8/2008 | Chakravarty et al. ............. | 707/6 |
| 2009/0299926 | A1 * | 12/2009 | Garrity et al. ................... | 706/14 |
| 2009/0327170 | A1 * | 12/2009 | Donati et al. ................... | 706/12 |
| 2010/0070509 | A1 * | 3/2010 | Li et al. .......................... | 707/747 |
| 2010/0106713 | A1 * | 4/2010 | Esuli et al. ..................... | 707/716 |
| 2011/0059853 | A1 * | 3/2011 | Emler et al. ...................... | 506/8 |
| 2011/0295902 | A1 * | 12/2011 | Mande et al. .................. | 707/794 |

OTHER PUBLICATIONS

Diaz, N. N., Krause, L., Goesmann, A., Niehaus, K. & Nattkemper, T. W. Tacoa: taxonomic classification of environmental genomic fragments using a kernelized nearest neighbor approach. BMC Bioinformatics 10, 56 (2009).*

Dudani, S. A. The Distance-Weighted k-Nearest-Neighbor Rule. IEEE Trans. Syst. Man. Cybern. SMC-6, 325-327 (1976).*

Gionis, A., Indyk, P. & Motwani, R. Similarity Search in High Dimensions via Hashing. In Int. Conf. Very Large Data Bases 518-529 (Morgan Kaufmann Publishers Inc., 1999).*

Jansen, A. & Van Durme, B. Efficient spoken term discovery using randomized algorithms. In Automatic Speech Recognition and Understanding (ASRU) 401-406 (2011).*

Rosequist, A. & Shen, H. Relative Searching Using an Ordered Token List. Inquiry: The University of Arkansas Undergraduate Research Journal. 9, 78-82 (2008).*

(Continued)

*Primary Examiner* — Soren Harward (74) *Attorney, Agent, or Firm* — Schwegman Lundberg & Woessner, P.A.

(57) ABSTRACT

In an implementation, a query signature corresponding to a query sequence based on a set of closest cluster centroids is generated. Based on the query signature, one or more target reference signatures from a plurality of reference signatures are identified. Further based on the one or more target reference signatures, a probable taxonomic group is identified and assigned to the query sequence.

21 Claims, 3 Drawing Sheets

(56) References Cited

OTHER PUBLICATIONS

"European Application Serial No. 11194858, European Search Report mailed Jul. 25, 2012", 9 pgs.

"European Application Serial No. 11194858, Office Action mailed Nov. 6, 2012", 2 pgs.

"European Application Serial No. 11194858, Response filed Feb. 11, 2013 to Office Action mailed Nov. 6, 2012", 22 pgs.

Brady, Arthur, et al., "Phymm and PhymmBL: metagenomic phylogenetic classification with interpolated Markov models", Nature Methods, 6, (2009), 673-676.

D'Auria, Giuseppe, et al., "IWoCS: analyzing ribosomal intergenic transcribed spacers configuration and taxonomic relationships", Bioinformatics, 22(5), (2006), 527-531.

McHardy, A. C, et al., "Accurate phylogenetic classification of variable-length DNA fragments.", Nat Methods, 4(1), (Jan. 2007), 63-72.

Mohammed, Monzoorul Haque, et al., "Sphinx—an algorithm for taxonomic binning of metagenomic sequences", Bioinformatics, 27(1), (2010), 22-30.

\* cited by examiner

TAXONOMIC CLASSIFICATION SYSTEM

CLAIM OF PRIORITY

This application claims the benefit of priority under 35 U.S.C. §119 of Sharmila Shekhar Mande, Indian Patent Application Serial Number 1363/MUM/2011, entitled "TAXONOMIC CLASSIFICATION SYSTEM," filed on Apr. 30, 2011, the benefit of priority of which is claimed hereby, and which is incorporated by reference herein in its entirety.

TECHNICAL FIELD

The present subject matter relates, in general, to the field of genomics and metagenomics and, in particular, taxonomic classification of genomic and metagenomic sequences.

BACKGROUND

The study of genetic material recovered directly from an environmental sample, by sequencing the genetic material, thereby bypassing isolation and cultivation step is referred to as metagenomics. Metagenomics provides information pertaining to taxonomic diversity, physiology and complex interactions among various microorganisms present in the environmental sample.

The genetic material obtained directly from the environmental sample is sequenced into a plurality of sequences, called metagenomic sequences. Each of these metagenomic sequences are then classified or cataloged into various taxonomic groups, such as kingdom, phylum, class, order, family, genus, or species. This whole process of classifying metagenomic sequences is called taxonomic classification or binning.

Taxonomic classification of metagenomic sequences, as the one mentioned above, helps in reconstructing the microbial composition of the environmental sample. It also provides information regarding evolutionary history and previously unrecognized physiological abilities of microbial communities specialized to live in a given environmental niche. Taxonomic classification not only catalogs known organisms, but also classifies new organisms to corresponding taxonomic groups for subsequent analyses. Precise taxonomic classification of metagenomic sequences is important since wrongly classified sequences may affect the accuracy of several downstream analyses, for example, sequence assembly, gene prediction, and functional annotation.

Researchers typically employ a variety of taxonomic classification techniques to classify metagenomic sequences. Conventional taxonomic classification techniques associate a sequence to a taxon if a feature of the sequence, such as sequence similarity or composition, is similar to reference sequences belonging to that taxon. However, such taxonomic classification techniques are either time consuming or prevent users from assessing the taxonomic diversity of environmental samples at appropriate taxonomic levels, i.e., such classification techniques are not specific and accurate.

SUMMARY

This summary is provided to introduce concepts related to taxonomic classification of metagenomic sequences, which are further described below in the detailed description. This summary is not intended to identify essential features of the claimed subject matter nor is it intended for use in determining or limiting the scope of the claimed subject matter.

Method(s) and a system(s) for taxonomic classification of a query sequence are described herein. In an implementation, a query signature corresponding to the query sequence based on a set of closest cluster centroids is generated. Based on the query signature, one or more target reference signatures from a plurality of reference signatures are identified. Further based on the one or more target reference signatures, a probable taxonomic group is identified and assigned to the query sequence.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

Typically, genetic material extracted directly from an environmental sample, i.e. metagenome, comprises a mixture of nucleic acids originating from different organisms present in that environment sample. The genetic material is sequenced to generate a plurality of metagenomic sequences, which are subsequently analyzed for estimating taxonomic diversity of the given environmental sample. For the purposes of discussion, metagenomic sequences, or 'metagenomic reads', that are to be analyzed may be interchangeably referred to as query sequences.

A variety of taxonomic classification techniques have been used for the classification of query sequences derived from various organisms present in a given an environmental sample into their corresponding taxonomic groups. A taxonomic group may be interchangeably referred to as a taxon. Conventional taxonomic classification techniques assign a taxon to a query sequence if features of the query sequence are similar to features of reference sequences belonging to that taxon. The accuracy and specificity of the given taxonomical classification technique depends upon the type of features selected and the heuristics employed to judge relatedness between query and reference sequences with respect to these features.

Higher level taxa, for example, taxa at the level of root, cellular organisms, and super-kingdom may be referred to as non-specific taxa, while lower level taxa, for example, taxa at the level of phylum, class, order, family, genus and below may be referred to as specific taxa. Accordingly, assignment of a query sequence to a specific taxon increases the specificity of the taxonomic classification technique. Conversely, assignment of a query sequence to a non-specific taxon decreases the specificity of the taxonomic classification technique.

One class of the conventional taxonomic classification techniques includes composition-based techniques, such as described in Phylopythia (Malardy et al., Accurate phylogenetic classification of variable length DNA fragments. Nature Methods, Volume 4, pages 63-72, 2007), TACOA (Diaz et al., TACOA—Taxonomic classification of environmental genomic fragments using a kernelized nearest neighbor approach, BMC Bioinformatics, Volume 10, page 56, 2009), and PhymmBL (Brady et al., Phymm and PhymmBL: Metagenomic phylogenetic classification with interpolated Markov models, Nature Methods, Volume 6, pages 673-676, 2009). These techniques classify a query sequence based on similarity of its compositional characteristics to those of reference sequences. The compositional characteristics may include, for example, guanine-cytosine (GC) content, oligonucleotide frequencies, etc. The GC content is the percentage of nucleobases in the query sequence, which are either guanine or cytosine, and the oligonucleotide frequency is the number of occurrences of an oligonucleotide of a given length in a query sequence.

The conventional composition-based techniques may not be robust enough to identify a taxon corresponding to a query sequence with a short sequence length, for example, less than 1000 base pairs. Such composition based techniques, usually, assign a majority of query sequences to non-specific taxa, for example, taxa at the level of root, cellular organisms, and super-kingdom.

Another class of the taxonomic classification techniques includes similarity-based techniques. The similarity-based classification techniques seek to identify a taxon corresponding to a query sequence by comparing the query sequence with every individual reference sequence stored in a database. For the purpose of comparing, the similarity based techniques may use alignment tools, such as Basic Local Alignment Search Tool (BLAST). Based on the comparison, information pertaining to alignment of the query sequence and the reference sequences is obtained. Accordingly, reference sequences that are homologous to the query sequence, i.e., suggesting a common ancestry or evolutionary origin with the query sequence, are analyzed to identify a taxon corresponding to the query sequence. Generally, similarity-based techniques have greater accuracy and specificity as compared to the composition-based techniques. However, the similarity-based techniques involve substantial computational time and resources in aligning a query sequence against each of the reference sequences stored in a database, such as a non-redundant (nr) database that contains more than 9 million sequences.

Thus, the conventional taxonomic classification techniques either involve considerable computational time and resources or are not efficient in terms of accuracy and specificity.

According to an embodiment of the present subject matter, methods and systems for taxonomic classification of query sequences are described herein. The taxonomic classification is associated with a reference database having a plurality of reference signatures corresponding to a plurality of reference sequences.

In one implementation, the reference sequences may be nucleic acid reference sequences, which may be clustered based on nucleotide compositional characteristics, such as tetranucleotide frequency. Alternatively, other nucleotide compositional characteristics, for example. GC content and or any other oligonucleotide frequency, may also be used. Further, each of the reference clusters may contain amino acid reference sequences corresponding to the nucleic acid reference sequences. In another implementation, the reference sequences may be amino acid reference sequences, which may be clustered using amino acid compositional characteristics, such as oligo-peptide frequencies. Further, the reference database may include coding or non-coding reference sequences or reference sequences having both coding and non-coding regions. As is known in the art, a coding sequence is a gene sequence that codes for a protein and its antithesis is a non-coding sequence. Likewise, a query sequence may also be a coding or non-coding sequence, or a sequence having a combination of both coding and non-coding regions.

In one implementation, a frequency vector for each of the reference sequences is determined and is referred to as reference vectors. The reference vectors and accordingly the reference sequences are grouped into corresponding reference clusters based on their compositional characteristics. For each reference cluster a cluster centroid is computed and the cluster centroids are tagged to the corresponding reference clusters. Further, for each reference sequence in the reference database a reference signature is generated. For the purpose, distances between each of the reference vectors and each of the cluster centroids are computed. For each reference vector, a set of closest cluster centroids are identified, based on the computed distances and accordingly a reference signature is generated. The set of closest cluster centroids may be determined such that no two reference sequences have similar reference signature. Subsequently, each reference sequence along with its source and its corresponding reference signature may be stored in the reference database.

Once, the reference signatures are generated, the reference signatures are sorted such that the reference sequences with similar reference signatures and therefore with similar phylogenetic origin fall in vicinity of one another. It will be understood that creation of the reference database is one time pre-processing step and may not be repeated every time a new query sequence is to be analyzed.

In one implementation, one or more query sequences to be analyzed are received. For identification of taxon corresponding to each of the query sequences, query signatures of all query sequences are generated in a way similar to the generation of the reference signatures. The query signatures are sorted with respect to the reference signatures, which are stored in the reference database. Upon sorting, for each query sequence, one or more target reference signatures are identified. The target reference signatures can be understood as the reference signatures, which are similar to the query signature. The target reference signatures are assigned a similarity score based on extent of similarity with respect to the query signature. In one example, the similarity between the reference signatures and the query signatures is indicative of compositional similarity between the query sequences and the reference sequences.

Further, each of the target reference signatures is assigned a taxonomic assignment flag (TA-flag) based on the similarity score assigned to the target reference sequence. The TA-flag represents a particular taxonomic level so that only taxa or clades of reference sequence lineage, which are either equal to or higher than the particular taxonomic level are considered for binning the query sequence. Based on the TA-flags associated with the target reference signatures, a taxonomic level from where a taxon may subsequently be selected for taxonomic classification of a query sequence is identified. Further, for each query sequence, a most common taxonomic group, belonging to a taxonomic level identified for respective query sequence, is selected. The most common taxonomic group can be understood as a taxon associated with a maximum number, i.e., a majority of the target reference signatures. For example, *Bradyrhizobium* is a genus level taxon and Alphaproteobacteria is an order level taxon. In another example, the most common taxonomic group associated with the target reference sequences may be the root level. In such cases, the query sequence may be categorized as unassigned. Further, a proportion of the target reference signatures having the most common taxonomic group is computed. Based on the computed proportion, the most common taxonomic group is identified as a probable taxonomic group to which the query sequence belongs and is assigned to the query sequence. The probable taxonomic group indicates a taxon to which the query sequence under consideration belongs.

According to the present taxonomic classification technique, the taxonomic assignment of query sequences is based on similarity between corresponding query signature and reference signatures instead of the nucleic acid or amino acid sequences. The signatures for the query and reference sequences are generated such that the signature similarity is indicative of the compositional similarity between the query sequences and the reference sequences. Further, the signatures are sortable such that a single step of sorting query and reference signatures together ensures that similar reference and query signatures are placed in the vicinity of each other thereby eliminating the exhaustive All-vs-All database search. Owing to aforementioned signature characteristics, the efficiency of the present taxonomic classification technique is considerably enhanced in terms of computational time and resources.

Furthermore, millions of query sequences generated through high-throughput sequencing techniques may be inputted together and all the taxonomic classification of the query sequences may be performed in a collective or simultaneous manner. Moreover, as will be shown using various test case scenarios, the accuracy and specificity of the present taxonomic classification technique is comparable to conventional similarity-based techniques.

While aspects of described systems and methods for the taxonomic classification of the metagenomic sequences can be implemented in any number of different computing systems, environments, and/or configurations, the embodiments are described in the context of the following exemplary system(s).

Exemplary Systems

Figure 1:
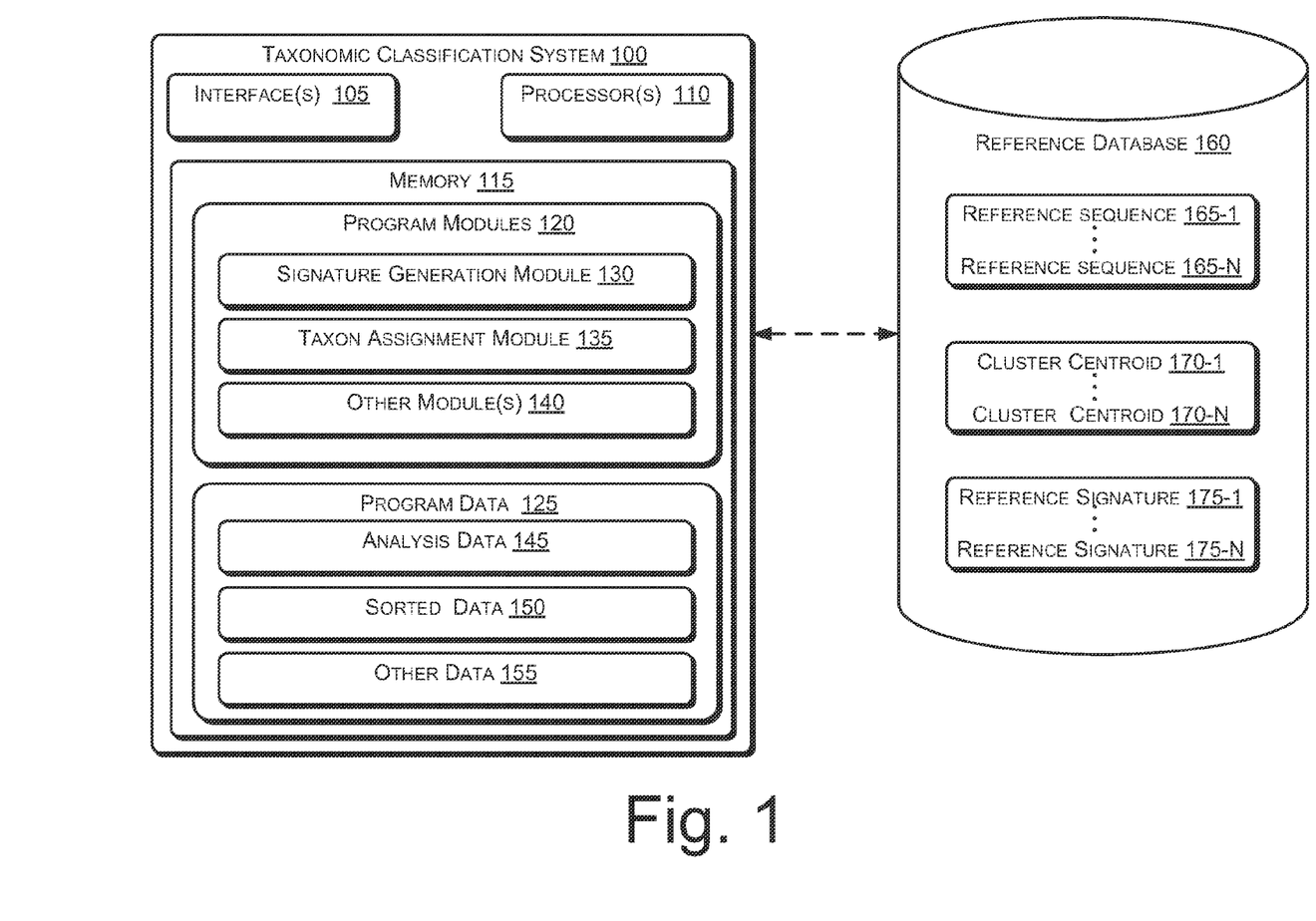
FIG. 1 illustrates an exemplary system for taxonomic classification of a query sequence, in accordance with an embodiment of the present subject matter.

FIG. 1 illustrates an exemplary taxonomic classification system 100, according to an implementation of the present subject matter. The taxonomic classification system 100 can be implemented in systems that include, but are not limited to, desktop computers, hand-held devices, multiprocessor systems, personal digital assistants (PDAs), laptops, network computers, cloud servers, minicomputers, mainframe computers, and the like. In one implementation, the taxonomic classification system 100 includes interface(s) 105, one or more processor(s) 110, and a memory 115 coupled to the processor(s) 110.

The interfaces 105 may include a variety of software and hardware interfaces, for example, interfaces for peripheral device(s), such as a keyboard, a mouse, an external memory, and a printer. Further, the interfaces 105 may enable the taxonomic classification system 100 to communicate with other devices, such as web servers and external databases. The interfaces 105 can facilitate multiple communications within a wide variety of networks and protocol types, including wired networks, for example local area network (LAN), cable, etc., and wireless networks such as Wireless LAN (WLAN), cellular, or satellite. For the purpose, the interfaces 105 may include one or more ports for connecting a number of computing systems with one another or to another server computer.

The processor 110 can be a single processing unit or a number of units, all of which could include multiple computing units. The processor 110 may be implemented as one or more microprocessors, microcomputers, microcontrollers, digital signal processors, central processing units, state machines, logic circuitries, and/or any devices that manipulate signals based on operational instructions. Among other capabilities, the processor 110 is configured to fetch and execute computer-readable instructions and data stored in the memory 115.

The memory 115 may include any computer-readable medium known in the art including, for example, volatile memory such as static random access memory (SRAM) and dynamic random access memory (DRAM), and/or non-volatile memory, such as read only memory (ROM), erasable programmable ROM, flash memories, hard disks, optical disks, and magnetic tapes. The memory 115 also includes program module(s) 120 and a program data 125.

The program modules 120, amongst other things, include routines, programs, objects, components, data structures, etc., which perform particular tasks or implement particular abstract data types. The program modules 120 further include a signature generation module 130, a taxon assignment module 135, and other module(s) 140. The other modules 140 may include programs that supplement applications on the taxonomic classification system 100, for example, programs in the operating system. On the other hand, the program data 125 serves, amongst other things, as a repository for storing data processed, received, and generated by one or more of the program modules 120. The program data 125 includes analysis data 145, sorted data 150, and other data 155. The other data 155 includes data generated as a result of the execution of one or more modules in the other modules 140.

In one implementation, the taxonomic classification system 100 is associated with a reference database 160. The reference database 160 can be either external or internal to the taxonomic classification system 100. The reference database 160 includes a plurality of reference sequences 165-1 . . . 165-N, hereinafter referred to as reference sequence(s) 165. The reference sequences 165 may be in the form of nucleic acid sequence or in the form of amino acid sequences. Additionally, the reference sequences 165 may contain coding sequences or non-coding sequences or sequences having both coding and non-coding regions. Further, the reference sequences may be selected from genomic sequences or protein sequences. Furthermore, the reference sequences may be derived from partially or completely sequenced genomes.

Further, the reference database 160 may be a pre-configured database, which includes the reference sequences 165 clustered into a plurality of reference clusters with each reference cluster having a particular set of reference sequences 165. For example, a first reference cluster may include reference sequences 165-1A to 165-1Z, a second reference cluster may include reference sequences 165-2A to 165-2Z, and so on.

Further, each of the reference clusters may have a corresponding cluster centroid 170. Thus, the reference database 160 may include a plurality of cluster centroid(s) 170-1 . . . 170-N. The reference database 160 may also include a plurality of reference signatures 175-1 . . . 175-N corresponding to the reference sequences 165. The reference signatures 175 may be stored in a manner such that the compositionally similar reference sequences 165 fall in the vicinity of each other. Further, each of the reference sequences 165 may be associated with the corresponding reference cluster and the reference signatures 175. Additionally, a source organism and an entire lineage from root level to the source organism may also be associated with the reference sequences 165.

Further, it will be understood that the various blocks, i.e., the reference sequences 165, the cluster centroids 170, and the reference signatures 175 depicted in the reference database 160 are only for the purpose of illustration and not as a limitation. The reference database 160 may store the reference sequences 165, the cluster centroids 170, and the reference signatures 175 in any form known in the art and may associate these blocks as known in the art.

In one implementation, the signature generation module 130 may categorize the reference sequences 165 into the reference clusters based on the compositional characteristics of the reference sequences 165. Although, the clustering of the reference sequences 165 is explained in considerable detail with reference to tetra-nucleotide frequency as a compositional characteristic, it will be appreciated that other compositional characteristics, for example, GC content or any other oligonucleotide frequencies may also be used for clustering of the reference sequences 165.

The signature generation module 130 computes frequencies of all possible tetra-nucleotides in each of the reference sequences 165 and accordingly generates a reference vector corresponding to each of the reference sequences 165. Reference vectors may be represented in the form of 256-dimensional vectors. Subsequently, the reference sequences 165, based on the corresponding reference vectors, may be classified into the reference clusters using conventional clustering techniques, such as k-means clustering technique in which n number of observations are partitioned into k number of clusters such that each observation belongs to a cluster with the nearest mean.

In an implementation, in order to form the reference clusters, the signature generation module 130 selects a predetermined number of reference clusters and the cluster centroids 170-1 . . . 170-N where each of the cluster centroids 170 corresponds to a reference cluster. For every reference vector, a closest cluster centroid 170 is determined and the reference sequence 165 corresponding to the reference vector is moved to the reference cluster corresponding to the closest cluster centroid 170. In this way, the reference sequences 165 with similar compositional characteristics are moved to same reference cluster.

The closest reference cluster for a reference sequence 165 may be determined based on a distance between a reference vector corresponding to the reference sequence 165 and each of the cluster centroids 170. The distance, for example, may be measured in terms of Euclidean metrics or non-Euclidean distance metrics, for instance, Manhattan distance (L1 norm), Cosine measure, Chebyshev distance, Minkowski distance, and Mahalanobis distance, Further, if the reference sequence 165 under consideration is moved to a reference cluster, the clusters centroids 170 are computed again. A cluster centroid 170 represents a mean value of the reference vectors corresponding to the reference sequences 165 present in a reference cluster. In one implementation, the process of forming the reference clusters can be performed repeatedly till the reference clusters become stable or some maximum number of iterations have been performed. Further, the cluster centroids 170 may be tagged to the corresponding reference clusters. The distribution of the cluster centroids 170 is optimal and can be considered to account for diversity that exists among currently known genomes. Additionally or alternatively, the signature generation module 130 may translate the reference sequences 165 into corresponding amino acid reference sequences and store the amino acid reference sequences in their respective reference clusters.

In one implementation, the cluster centroids 170 may be stored in an orderly manner. For example, a cluster centroid, say the cluster centroid 170-1, may be randomly chosen and numbered one. The distances from this centroid one to all the remaining cluster centroids 170 may be computed and the closest cluster centroid, say, the cluster centroid 170-2 may be numbered as two. Now, a centroid (referred as resultant centroid) of the cluster centroid 170-1 and the cluster centroid 170-2 is determined. Further, distances from this resultant centroid to all the remaining cluster centroids 170 is computed and a resultant closest cluster centroid may be numbered as three. Now a new centroid representing all three previously numbered cluster centroids 170, i.e., 'centroid one', 'centroid two', and 'centroid three' is determined and distances from that resultant centroid to all the remaining cluster centroids 170 are calculated and the procedure may be repeated in an iterative manner until all the original cluster centroids 170 are numbered.

Such procedure ensures that the cluster centroids 170 that are spatially close get closely numbered. For example "centroid 9" will be closer to the "centroid 10" or "centroid 11" or "centroid 56" compared to "centroid 607" or "centroid 1007". Such orderly numbering of the cluster centroids 170 ensures that sorting signatures generated from these cluster centroids 170 will place compositionally similar reference sequences 165 together.

In order to generate the reference signatures 175, for every reference vector, a set of closest cluster centroids are identified. The set of the closest cluster centroids may include a predetermined number of cluster centroids 170. Further, the set may be big enough to ensure that each reference sequence 165 has a unique reference signature 175 and at the same time small enough to save on computational time and resources. In one example, the predetermined number of closest cluster centroids is twelve. The predetermined number of closest cluster centroids may be identified based on a distance, such as, the Manhattan distance between the reference vector and the cluster centroids 170. Accordingly, a set of the closest cluster centroids includes the cluster centroids 170, which are at a least distance from the reference vectors are identified.

Further, the signature generation module 130 may order the closest cluster centroids based on their distances from the reference vector to result in a sequence-specific continuous string, referred to as the reference signature 175. In one implementation, the cluster centroids 170 may be placed in an ascending order, i.e., in an increasing order of the distance from the reference vector to generate the reference signature 175. In said implementation, a first cluster centroid 170 is closest, i.e., at a least distance from the reference vector and a twelfth cluster centroid 170 is farthest from the reference vector. One example of a reference vector computed corresponding to a reference sequence is provided below:

| 1st Dimension | 2nd | 3rd | 4th | 5th | 6th | ... | 256th Dimension |
|---|---|---|---|---|---|---|---|
| [0.020677 | 0.006579 | 0.01316 | 0.01692 | 0.00752 | 0.000094 | | 0.007519] |

Further, twelve closest cluster centroids may be identified as, 143, 135, 144, 315, 320, 140, 174, 134, 137, 177, 132, and 314. These twelve cluster centroids 170 may be arranged in ascending order of their distances from the reference vector to give the reference signature 175:

01430135014403150320014001740134013701770132 0314
For the purposes of illustration, each of the cluster centroids 170 is four characters long in length. It will be understood that the any other way of representation may also be used.

Thus, for each of the reference vectors, effectively the reference sequences 165, corresponding reference signature 175 is generated. Further, the signature generation module 130 may sort the reference sequences 165 such that reference sequences 165 with similar reference signatures 175 get in close proximity to each other. Such sorting ensures that the compositionally similar reference sequences 165 fall in the vicinity of each other. The sorted reference signatures 175 along with their organism of origin may then be stored in a single text file, where each line represents a reference sequence 165 in the form of its reference signature 175 and organism name. For example, the sorted file includes the reference signatures 175 compositionally similar to a reference signature, say, reference signature 175-1, in lines surrounding (above and below) the reference signature 175-1. In one implementation, the reference signatures 175 may be sorted in lexical order to place the lexically similar and therefore compositionally and phylogenetically related reference signatures 175, or to say, reference sequences 165, in the vicinity of each other. The sorting may be understood with the help of the following example, Before lexical sort:

| | |
|---|---|
| 00310548053205490030053300290550002605350395 0501 | Organism_A |
| 02680266023801670258026502640260036202480255 0259 | Organism_B |
| 03950380039403860531037705320388049603960530 0387 | Organism_C |
| 00010002000300090019132910611055108313240010 0471 | Organism_D |
| 07130712093807040710079004152050716083505610 0714 | Organism_E |
| 09450950094209440948072709411113139205830947 0946 | Organism_F |
| 08250823060208260592060306010824059008220593 1123 | Organism_G |
| 16811682037413631038037303961351030202990305 0376 | Organism_H |
| 00010002000300090720113111380004052608720575 0554 | Organism_D |
| 09450950094209440948072709411113139205830947 0946 | Organism_F |
| 02680266023801670265025502600360224825802640 0249 | Organism_B |
| 00010455045705221051052308760452001010541055 0009 | Organism_D |
| 16811682135110381363037413650305030203730396 0299 | Organism_H |

After lexical sort:

| | |
|---|---|
| 00010002000300090019132910611055108313240010 0471 | Organism_D |
| 00010002000300090720113111380004052608720575 0554 | Organism_D |
| 00010455045705221051052308760452001010541055 0009 | Organism_D |
| 00310548053205490030053300290550002605350395 0501 | Organism_A |
| 02680266023801670258026502640260036202480255 0259 | Organism_B |
| 02680266023801670265025502600360224825802640 0249 | Organism_B |
| 03950380039403860531037705320388049603960530 0387 | Organism_C |
| 07130712093807040710079004152050716083505610 0714 | Organism_E |
| 08250823060208260592060306010824059008220593 1123 | Organism_G |
| 09450950094209440948072709411113139205830947 0946 | Organism_F |
| 09450950094209440948072709411113139205830947 0946 | Organism_F |
| 16811682037413631038037303961351030202990305 0376 | Organism_H |
| 16811682135110381363037413650305030203730396 0299 | Organism_H |

In one implementation, the reference database 160 may include multiple sub-databases based on the length of the reference sequences 165 and the query sequences. For example, the reference database 160 may include a first sub-database having reference sequences 165 with length of 1000 base pairs (bp) and second sub-databases having the reference sequences 165 of length 400 bp. For these two sub-databases, two different sets of cluster centroids 170 and two different sorted files having the reference signatures 175 are generated. The cluster centroids 170 and reference signatures 175 corresponding to first sub-database, i.e., corresponding to 1000 bp long reference sequences may be employed automatically for the query sequences 800 by long in length and for the query sequences with 400 bp or 250 bp or 100 bp read lengths, the second sub-database may be employed automatically.

In one implementation, one or more query sequences are provided to the taxonomic classification system 100. The input file including the query sequences may be provided in any one of the nucleic or amino acid sequence file formats. For example, the input file may be provided in PASTA format. The input file may contain either single or multiple query sequences. In an example, in case of the reference database 160 having multiple sub-databases, the signature generation module 130 may also determine read length of the query sequences and accordingly select a sub-database. The signature generation module 130 is configured to generate a query signature for each of the query sequences. As mentioned while describing the generation of the reference signatures 175, a vector, in the present case, a query vector is generated for each of the query sequences. The query vector may be generated based on the frequencies of all possible tetra-nucleotides in the corresponding query sequence. The query vectors may be stored as 256-dimensional vectors. It will be understood that compositional characteristics used for generating a query vector would be similar to the compositional characteristics used for generating a reference vector.

Further, for each of the query sequences, distances, for example, Manhattan distances (L1 norm), Cosine measure, Chebyshev distance, Minkowski distance, and Mahalanobis distance between corresponding query vectors and the cluster centroids 170 are computed. Based on the computed distances, the set of the closest cluster centroids is identified. The closest cluster centroids may be arranged in a specific order, say, in ascending order of distances from the query vector. In other words, a cluster centroid from the set of the closest cluster centroids 170, at a least distance from the query vector is kept first and then the second closest and so on. Thus, for each of the query sequences, the closest cluster centroids are ordered to generate query signatures. The query vectors and query signatures may be stored in the analysis data 145 for further analysis.

In one implementation, the query signatures may be merged with the reference signatures 175. For example, the reference signatures 175 and the query signatures may be merged and stored in the sorted data 150. Accordingly, if there were three million reference signatures 175 and ten thousand query signatures, then these ten thousand query signatures may be merged with the three million reference signatures 175 to give in total three million and ten thousand signatures.

Upon merging, all the signatures, the reference and the query signatures, stored in the sorted data 150 may be sorted, for example, in lexical order to place the query signatures in the regions surrounded (above and below) by lexically similar and therefore compositionally and phylogenetically related reference signatures 175, or to say, reference sequences 165. Thus, for all the query signatures and in turn the query sequences, compositionally similar reference signatures 175 and in turn reference sequences 165 are identified with single sorting step in one go without having to separately search each one of the query sequences against each of the reference sequences 165. Such a sorting of the query signatures, which places the query signatures in the vicinity of the phylogenetically related reference signatures 175 considerably reduces computational time and resources.

Subsequent to sorting, for each query signature, the taxon assignment module 135 identifies one or more target reference signatures, i.e., the reference signatures 175, which are compositionally similar to the query sequence. For example, n reference signatures 175 lying on either side of the query signature may be identified as target reference signatures. In one implementation, the target reference signatures may be stored in the analysis data 145. The number of target reference signatures selected for the given query signature can vary with the length of query and reference sequences 165. For example, for the query sequence with the read length 800 base pairs, the number of target reference signatures is 26, while for the query sequence with read length of 400 and 250 bp, the number of target reference signatures is 40 and for the query sequence with read length of 100 bp, the number of target reference signatures is 52. It will be understood that the computation of the number of target reference signatures with even distribution of the reference signatures 175 on either side of a query signature is only for the purposes of illustration and not as a limitation.

For the sake of clarity, foregoing description is explained with respect to a single query sequence or to say a single query signature, however, it will be understood that the taxonomic classification of rest of the query sequences may be carried out in a similar manner. Further, for every target reference signature, the taxon assignment module 135 computes a similarity score based on an extent similarity between the target reference signature and the query signature. The similarity score can be computed based on a positional match of the cluster centroids 170 in both the query signature and the target reference signatures.

For example, consider a case where the signatures, which may be query or reference, are generated by placing the closest cluster centroids in ascending order of the distances from the respective vectors. In said example, since in a signature the first cluster centroid will be closest to the respective vector, and the proximity of the cluster centroids 170 in a signature to a corresponding vector decreases as one proceeds towards the end of the signature, the match between the first cluster centroid in a target reference signature with respect to the query signature (also referred to as first centroid match) is assigned the highest positional weightage in scoring, the second cluster centroid match has relatively less weightage and the last cluster centroid match has the least. Thus, the cluster centroid weightages are progressively down weighted. The similarity score for an individual target reference signature is computed as the collective sum of the positional scores obtained for all cluster centroid positions.

Such a scoring scheme ensures that those target reference signatures that are compositionally similar to the query signatures have higher similarity score compared to other target reference signatures. In one example, where a signature includes twelve closest cluster centroids arranged in an ascending order of the distances from respective vectors, the maximum similarity score that is assigned to a target reference signature for having an exact signature match with query signature is 78. In said example, a first centroid match may be assigned a weightage of 12, a second centroid match may be assigned a weightage of 11, and accordingly a last centroid match, in this example, a twelfth centroid match may be assigned a weightage of 1. In case of mismatch no weightage is given and accordingly the similarity score reduces. It will be understood that higher the similarity score of the target reference signature, greater is the compositional similarity between the query sequence and the target reference sequence.

In one implementation, the taxon assignment module 135 is further configured to compute a value of a 'taxonomic assignment flag' (TA-flag) for each of the target reference signatures. The values of the TA-flags for the target reference sequences may be computed based on respective similarity score. The TA-flag represents a particular taxonomic level so that only taxa or clades of reference sequence lineage, which are either equal to or higher than the particular taxonomic level are considered for binning the query sequence. In one example, the TA-flag may be assigned to the target reference sequences with 800 base pairs (bp) based on following exemplary table (Table 1):

TABLE 1

| Similarity Score Range | TA-Flag | Taxa/Clades of Reference Sequence Considered |
|---|---|---|
| 33-78 | 0.10 | Genus, Family, Order, Class, Phylum, |
| 28-33 | 0.20 | Order, Class, Phylum, Superkingdom |
| 23-28 | 0.25 | Class, Phylum, Superkingdom |
| <23 | 0.40 | Root |

As it can be seen, with the increase in similarity score, value of the TA-flag decreases and lower level taxa/clades are considered for taxonomic classification of the query sequences. Further, the values assigned to the TA-flag with respect to the similarity score may vary based on the length of the query sequence and the target reference sequences. For example, with the query sequences of length 100 bp, the target reference signatures with the similarity score in the range 33-78 are assigned a TA-flag with value 0.10.

Based in part on the value of the TA-flags of all the target reference signatures associated with a query signature, a taxonomic level for taxonomic classification of that query sequence is determined. Thus, it may be determined if a threshold TA-flag criterion is met or not. In one implementation, the tower most taxonomic level from where a particular taxon is selected for the query sequence is dictated by the TA-flags. For example, referring to the table 1, the lineage of a reference sequence with a TA-flag value 0.10 is considered from genus level, while for the TA-flag with value 0.20, the lineage is considered from the order level and for the TA-flag with value 0.25, the lineage is considered from the class level.

In one implementation, the taxon assignment module 135 initiates the taxonomic classification of the query sequence at the genus level. However, it will be understood that the taxonomic classification may be initiated at any other level as well. In one example, to initiate taxonomic classification of a query sequence at a given taxonomic level, the taxon assignment module 135 is configured to determine a proportion of the target reference signatures that have TA-flags corresponding to the given or lower taxonomic levels. The taxon assignment module 135 may compare the proportion of the target reference signatures having the TA-flags corresponding to the given taxonomic level or a lower taxonomic level with a threshold TA-flag proportion.

For example, the taxonomic classification may be initiated at the class level. In said example, all the TA-flags that correspond to class level and lower taxonomic levels, i.e., order, family, and genus, are also considered. Thus, according to table 1, the target reference signatures with TA-flag values 0.10, 0.20, and 0.25 are considered for computing a proportion of the target reference signatures having TA-flags corresponding to the class level. Upon failure to meet the threshold TA-flag proportion, the taxonomic classification starts from an immediate higher taxonomic level. For instance, consider the threshold TA-flag proportion is 66% and the taxonomic classification is initiated at genus level. If it is determined that only 50% of the target reference signatures have TA-flags as 0.10 then it may be determined that the threshold TA-flag proportion criterion is not satisfied and the taxonomic classification is not initiated at the genus level but at a next higher taxonomic level, say, family level, is selected. Further, if TA-flag proportion for a TA flag is not satisfied, the taxon assignment module 135 may automatically consider a taxonomic level corresponding to the next higher TA-flag value. Further, if it is determined that the next higher level is root, the query sequence under consideration is classified as unassigned and no taxon is assigned to the query sequence.

Once the threshold TA-flag proportion criterion is met, i.e. the threshold proportion of the target reference signatures converge to a common TA-flag and a taxonomic level is identified, the query sequence may be assigned a particular taxon, i.e., a particular taxonomic group from the identified taxonomic level or a taxonomic level higher than the identified taxonomic level. In order to determine a taxon from the identified taxonomic level, the taxon assignment module 135 determines a proportion of the most common taxonomic group, hereinafter referred to as most common taxon. In order to determine the most common taxon, individual taxa of the target reference sequences or signatures at that taxonomic level are considered and the taxa appearing maximum number of times is determined as the most common taxon. For example, if the taxonomic level meeting the threshold TA-flags criterion is phylum, then a taxon, say, Proteobacteria may be identified as the most common taxon.

Further, the most common taxon may be identified as a probable taxonomic group and may be assigned to the query sequence corresponding to the query signature under analysis, based on the proportion of the most common taxon. Thus, based on the proportion of most common taxon, it may be determined if a threshold taxon proportion criterion is met or not. In one example, if the proportion of the most common taxon is greater than the threshold taxon proportion, it may be determined that the threshold proportion criterion is met and the most common taxon is the probable taxonomic group. Accordingly, the query sequence is assigned a taxon corresponding to the most common taxon. However, if it is determined that the proportion of the most common taxon is lesser than the threshold taxon proportion, then the immediate higher taxonomic level is identified.

For example, consider that taxonomic level, order, was previously identified as the taxonomic level with threshold TA-flag proportion. However, if for the order level, the threshold taxon proportion criterion is not met, next higher taxonomic level, i.e., class level is selected. Now, it is determined, if proportion of the most common taxon, from the taxonomic level class, is greater than the threshold taxon proportion. If so, the query sequence is assigned a taxon corresponding to the most common taxon from the class level.

Further, if the threshold taxon criteria is still not met at the immediate higher taxonomic level, aforementioned process iteratively shifts to immediate higher taxonomic levels. Upon failure to meet the threshold taxon proportion criteria even at superkingdom level, the query sequence may be moved to 'Unassigned' bin. Further, the results of the analysis performed by the taxon assignment module 135 may be stored in the analysis data 145.

It will be understood that the threshold TA-flag proportion and the threshold taxon proportion may vary based on a sequence length of the query sequences. For example, the threshold taxon proportion for query sequence of read length 800 bp and 250 bp may be 75%, while the threshold taxon proportion for query sequence of read length 400 bp may be 72% and the threshold taxon proportion for query sequence of read length 100 bp may be 77%.

The present taxonomic classification technique substantially reduces the amount of wrong taxonomic assignments that are inherently associated with composition based binning algorithms. In the present taxonomic classification a query sequence with compositionally similar and taxonomically uniform target reference sequences has a higher probability of getting assigned to a specific lower rank taxon/clade and the one with diverse and compositionally distant target reference sequences is likely to be assigned to a non-specific higher taxon/clade. Further, the present technique considerably reduces computational time and resources.

Validation and Results

For the purpose of validation, a modified reference database 160 was created, wherein reference sequences 165 corresponding to 300 randomly selected genomes from 952 genomes were removed prior to creating clusters in the reference database 160 to mimic a metagenomic scenario. Tracing of the taxonomic lineage of these 300 genomes revealed complete removal of certain chides from the reference database 160. The modified reference database 160 included two sets of reference sequences 165, one set where reference sequences 165 were of length 1000 bp and the other set had reference sequences 165 of length of 400 bp. The k-means clustering of reference sequences 165 generated from whole genomes of 952 microbes at a splicing length of 1000 bp gave rise to 1749 cluster centroids 170 whereas those at splicing length of 400 bp got clustered into 2136 cluster centroids 170. Further, k-means clustering of above mentioned reference sequences 165 after the removal of sequences belonging to 300 randomly selected genomes resulted in 1035 cluster centroids 170 at 1000 bp reference read length and 1638 cluster centroids 170 at 400 bp read length. The cluster centroids 170 and reference signatures 175 of 1000 bp long reference sequences constitute the sub-database 'RD1000' whereas the cluster centroids 170 and reference sequences 165 of 1000 bp long reference sequences, obtained after the removal of reference sequences 165 corresponding to 300 genomes, constitute the modified sub-database 'modified RD1000'. Similarly, the cluster centroids 170 and reference signatures 175 of 400 bp long reference sequences 165 constitute the sub-database RD400 whereas the cluster centroids 170 and reference sequences 165 of 400 bp long reference sequences 165 obtained after the removal of reference sequences 165 corresponding to 300 genomes constitute the modified sub-database 'modified RD400'. For query sequences of 800 bp in length, the modified RD1000 was employed whereas for query sequences of 400 bp or 250 bp or 100 bp read lengths, the modified RD400 was employed automatically. The final reference database 160, RD1000, consists of approximately 3.5 million reference sequences 165 with unique reference signatures 175 and RD400 is comprised of around 9 million reference sequences 165 and corresponding reference signatures 175. On the other hand, modified RD1000 contains around 2 million reference sequences 165 and their unique reference signatures 175 and similarly modified RD400 consists of approximately 5.3 million reference sequences 165 with their corresponding reference signatures 175.

Further, the binning efficiency of the present taxonomic classification technique was validated with reference to four different simulated test datasets having different read lengths. Depending on the lengths of the query sequences, the query sequences were divided into four validation data sets, termed as, Sanger data set, 454-400 data set, 454-250 data set, and 454-100 data set. The modified reference database 'modified RD1000' is used with Sanger dataset and 'modified RD400' with the three 454 datasets. Each of these data sets contained 35,000 query sequences. The query sequences constituting these four data sets simulated typical sequence lengths and error models obtained from commonly used sequencing techniques.

For example, query sequences constituting, the Sanger data set had read length or sequence length centered around 800 base pairs, 454-400 data set had sequence length centered around 400 base pairs, 454-250 data set had sequence length centered around 250 base pairs, and 454-100 data set had sequence length centered around 100 base pairs. Further, the Sanger data set simulated reads or sequences obtained using Sanger sequencing technology; 454-400 data set simulated sequences obtained using 454-GS-FLX-Titanium sequencing technology; 454-250 data set simulated sequences obtained using 454-GS-FLX-Standard sequencing technology, and 454-100 data set simulated sequences obtained using 454-GS20 sequencing technology.

As mentioned earlier, assignment of query sequences to taxa at the level of phylum or below is considered specific, while those above the level of phylum are considered non-specific. Assignment of a query sequence to a taxon that either corresponds to its source organism or to a taxon that lies in the path from the root to the taxon corresponding to the source organism of the query sequence, may be referred to as "correct". Likewise, assignment of a query sequence to a taxon that does not lie in the path from the root to the taxon corresponding to the source organism, may be referred to as "wrong". Further, those query sequences not satisfying threshold criteria, i.e., the query sequences that display weak signature similarity and thereby compositional similarity with their surrounding reference signatures 175 in the lexicographically sorted modified reference database 160 are classified as "unassigned". Furthermore the reference database 160 consists of reference signatures 175 corresponding to their respective reference sequences 165. These reference signatures 175 not only capture compositional characteristics of the nucleotide sequences of reference sequences 165 but also enable the query signature search across the reference database 160 with a single and simple step of lexical sorting.

Following tables 2a, 2b, 2c, and 2d depict comparison of the taxonomic assignment of query sequences in validation data sets obtained using the present taxonomic classification technique, according to one implementation of the present subject matter, and conventional taxonomic classification technique, for example, SPHINX (Monzoorul et al., SPHINX—an algorithm for taxonomic binning of metagenomic sequences. Bioinformatics, Volume 27, pages 22-30, 2010), TACOA, and MEGAN (Huson et al., MEGAN analysis of metagenomic data. Genome Research, Volume 17, pages 377-386, 2007), for Sanger data set, 454-400 data set, 454-250 data set and 454-100 data set, respectively. The "modified RD1000" and "modified RD400" are the reference databases 160 used for validation.

TABLE 2a

| Assignment Category/Taxon | Percentage of Sequences Assigned: Sanger Dataset | | | |
|---|---|---|---|---|
| | Present Technique | MEGAN | SPHINX | TACOA |
| Non-Specific* Levels | 33.84 | 16.33 | 14.44 | 56.9 |
| Specific# Levels | 48.39 | 35.73 | 55.76 | 7.92 |
| Phylum | 26.38 | 8.07 | 23.38 | 7 |
| Class | 5.25 | 7.56 | 12.04 | 0 |
| Order | 7.07 | 4.19 | 0 | 0.72 |
| Family | 1.35 | 6.2 | 12.26 | 0 |
| Genus & Lower | 8.33 | 9.7 | 8.08 | 0.2 |
| Total Correct | 82.23 | 52.06 | 70.2 | 64.82 |
| Wrong | 9.4 | 35 | 5.31 | 22.13 |
| Unassigned | 8.37 | 12.55 | 24.49 | 13.05 |

TABLE 2b

| Assignment Category/Taxon | Percentage of Sequences Assigned: 454-400 Dataset | | | |
|---|---|---|---|---|
| | Present Technique | MEGAN | SPHINX | TACOA |
| Non-Specific* Levels | 39.01 | 10.4 | 13.69 | 48.2 |
| Specific# Levels | 40.3 | 30.7 | 46.7 | 7.7 |
| Phylum | 28.99 | 10.9 | 21.15 | 4.88 |
| Class | 2.85 | 5.4 | 4.7 | 1.11 |
| Order | 2.83 | 2.94 | 0 | 0.61 |
| Family | 3.35 | 4.17 | 11.95 | 0 |
| Genus & Lower | 2.29 | 7.29 | 8.89 | 1.09 |
| Total Correct | 79.31 | 41.1 | 60.39 | 55.9 |
| Wrong | 9.84 | 38.7 | 12.03 | 26.6 |
| Unassigned | 10.85 | 20.2 | 27.58 | 15.9 |

TABLE 2c

| Assignment Category/Taxon | Percentage of Sequences Assigned: 454-250 Dataset | | | |
|---|---|---|---|---|
| | Present Technique | MEGAN | SPHINX | TACOA |
| Non-Specific* Levels | 39.23 | 14.07 | 11.49 | 46.82 |
| Specific# Levels | 38.15 | 27.19 | 36 | 6.81 |
| Phylum | 28.75 | 7.48 | 14.9 | 4.46 |
| Class | 2.31 | 4.39 | 4.97 | 1.09 |
| Order | 2.44 | 3.3 | 0 | 0.51 |
| Family | 2.83 | 3.84 | 9.19 | 0 |
| Genus & Lower | 1.82 | 8.19 | 6.94 | 0.75 |
| Total Correct | 77.38 | 41.26 | 47.49 | 53.63 |
| Wrong | 10.71 | 22.29 | 7 | 27.99 |
| Unassigned | 11.91 | 36.45 | 45.51 | 18.39 |

TABLE 2d

Percentage of Sequences Assigned: 454-100 Dataset

| Assignment Category/Taxon | Present Technique | MEGAN | SPHINX | TACOA |
|---|---|---|---|---|
| Non-Specific* Levels | 48.09 | 5.74 | 13.51 | 40.72 |
| Specific# Levels | 26.81 | 14.07 | 24.43 | 4.33 |
| Phylum | 23.85 | 5.06 | 17.49 | 2.65 |
| Class | 0 | 1.81 | 0.22 | 0.76 |
| Order | 1.19 | 0.34 | 0 | 0.45 |
| Family | 0.83 | 1.66 | 4.46 | 0 |
| Genus & Lower | 0.94 | 5.21 | 2.26 | 0.47 |
| Total Correct | 74.9 | 19.81 | 37.94 | 45.05 |
| Wrong | 10.61 | 10.11 | 7.46 | 31.6 |
| Unassigned | 14.49 | 70.09 | 54.61 | 23.29 |

As can be seen from aforementioned tables, the correct assignments made by the present taxonomic classification technique at specific levels is comparable to the specificity of the conventional similarity based taxonomic classification techniques (MEGAN) and hybrid classification (SPHINX) techniques. Further, the specificity of the present taxonomic classification technique is higher than the conventional composition based classification techniques (TACOA). Further, it may also be observed that the total number of correct assignments made by the present classification technique is better than the conventional classification techniques, thus indicating that the present classification technique has accuracy better than the conventional classification techniques. The present taxonomic classification technique displayed only a 7 percent drop in binning accuracy from Sanger to 454-100 dataset as opposed to 30, 46 and 62 percent drops of TACOA, SPHINX and MEGAN respectively, thereby indicating that present taxonomic classification technique has maintained more consistent binning accuracies with decreasing read length when compared to the rest.

Further, computational time taken by the present taxonomic classification technique is substantially lower than the conventional taxonomic classification techniques, and the same is illustrated by way of table 3. Table 3 depicts average time taken for taxonomic classification of 10,000 query sequences using the present taxonomic classification technique and the conventional similarity based classification technique, MEGAN, SOrt ITEMS (Monzoorul et al., SOrt-ITEMS: sequence orthology based approach for improved taxonomic estimation of metagenomic sequences. Bioinformatics, Volume 25, pages 1722-1730, 2009) and SPHINX. These time estimates were obtained using a desktop computer with Intel Xeon quad core processor and 4 GB random access memory (RAM). As explained previously, the overall time taken to bin 10,000 reads of 800 bp long is with respect to RD1000 and the time taken to bin reads of lengths 400 bp, 250 bp and 100 bp is with respect to RD400.

TABLE 3

Overall time taken for binning 10000 reads in minutes

| Read Length | TWARIT | SPHINX | MEGAN | SOrt ITEMS |
|---|---|---|---|---|
| 800 bp | 3 | 97 | 366 | 381 |
| 400 bp | 5 | 69 | 323 | 338 |
| 250 bp | 5 | 51 | 305 | 340 |
| 100 bp | 5 | 32 | 265 | 270 |

Table 3 shows that the present taxonomic classification technique achieves as much as 100 fold reduction in overall binning time at 800 bp read length and a 60 to 65 fold reduction at 100-400 bp read lengths compared to MEGAN and SOrt ITEMS. Further, it can be deduced from table 3 that the present taxonomic classification technique is approximately 30 times faster at Sanger read lengths and around 6 to 14 times faster at 454 read lengths when compared to SPHINX, which is considered to be the most rapid among algorithms which involve BLAST at some stage in their binning operation.

The results indicated in table 3 together with those of binning accuracy and specificity (given in Table 2) demonstrate the ability of the present taxonomic classification technique against the reference dataset to greatly reduce the time associated with conventional similarity-based binning without losing much efficiency in terms of accuracy and specificity.

Figure 2:
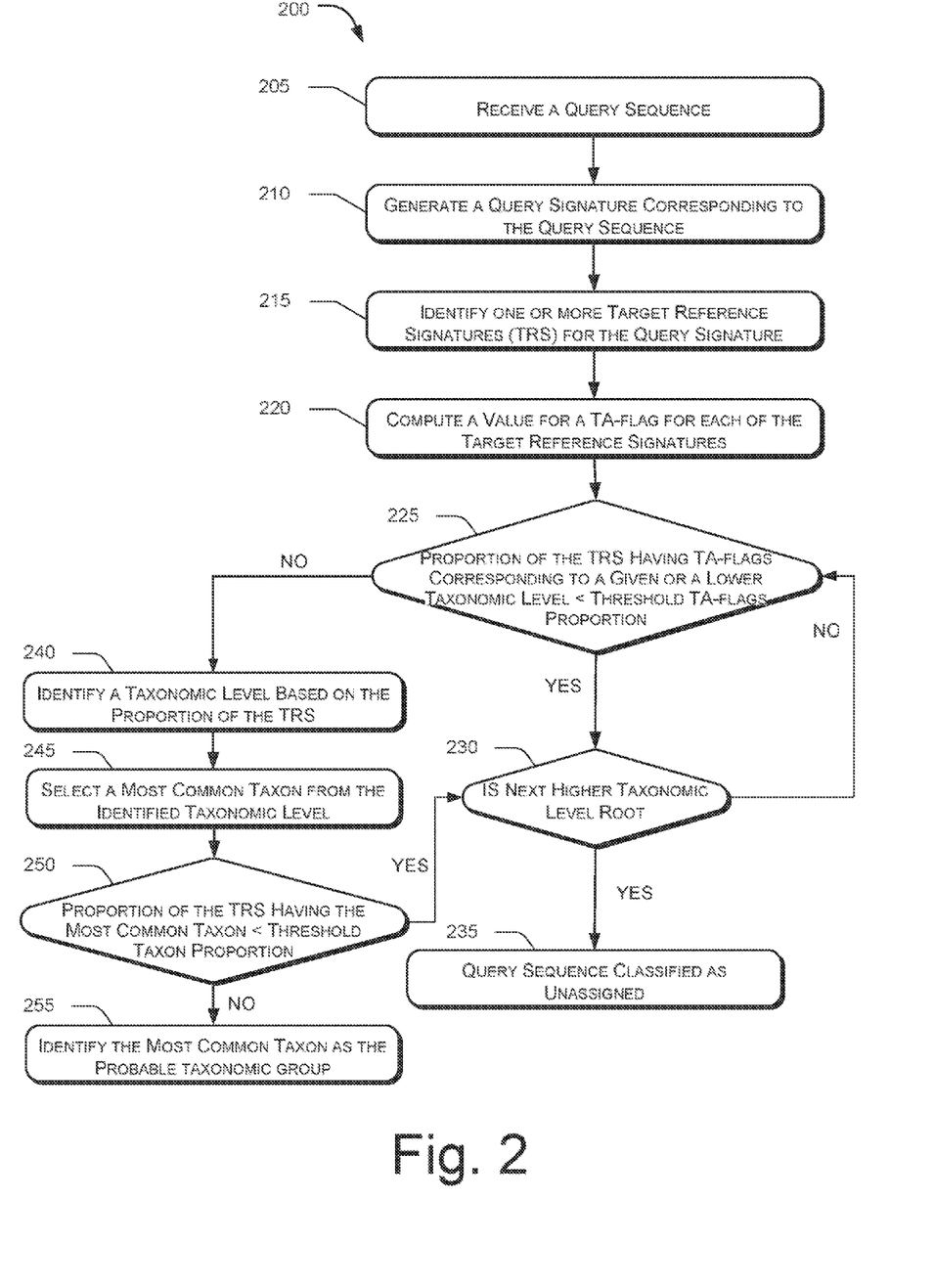
FIG. 2 illustrates an exemplary method for taxonomic classification of a query sequence, in accordance with an implementation of the present subject matter
Figure 3:
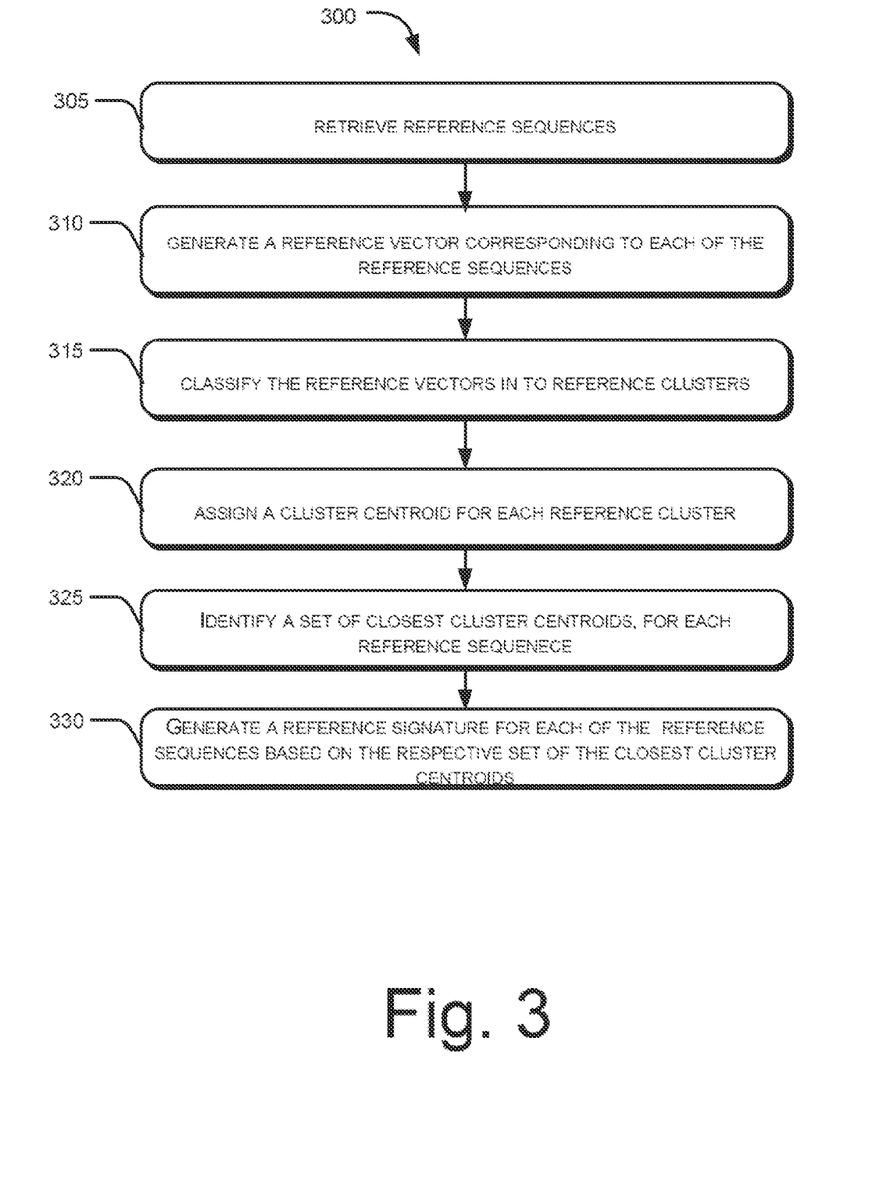
FIG. 3 illustrates an exemplary method to generate reference signatures, in accordance with an implementation of the present subject matter.

FIG. 2 illustrates an exemplary method 200 for taxonomic classification of one or more query sequences and FIG. 3 illustrates an exemplary method 300 for generation of reference signatures, in accordance with one or more implementations of the present subject matter.

The exemplary methods may be described in the general context of computer executable instructions. Generally, computer executable instructions can include routines, programs, objects, components, data structures, procedures, modules, functions, etc., that perform particular functions or implement particular abstract data types. The methods may also be practiced in a distributed computing environment where functions are performed by remote processing devices that are linked through a communications network. In a distributed computing environment, computer executable instructions may be located in both local and remote computer storage media, including memory storage devices.

The order in which the methods are described is not intended to be construed as a limitation, and any number of the described method blocks can be combined in any order to implement the method, or an alternative method. Additionally, individual blocks may be deleted from the methods without departing from the spirit and scope of the subject matter described herein. Further, the methods can be implemented in any suitable hardware, software, firmware, or combination thereof.

Referring to FIG. 2, which illustrates the method 200 for taxonomic classification of one or more query sequences, it will be understood that though the method 200 is presently provided for a query sequence, the same method can also be implemented for a plurality of query sequences without deviating from the scope of the present subject matter.

At block 205, a query sequence is received. The query sequence may be a genomic sequence or a metagenomic sequence. Further, the query sequence may be in the form of a nucleic acid sequence or an amino acid sequence. In one implementation, the query sequence is received by the signature generation module 130. Further, it will be understood that multiple query sequences may be inputted together as well.

At block 210, a query signature corresponding to the query sequence is generated. For example, the signature generation module 130 on receiving the query sequence generates a query signature corresponding to the query sequences. In one implementation, to generate the query signature, a query vector is generated for the query sequence, based on a composition characteristic, such as tetra-nucleotide frequency, of the query sequence.

For each query vector, a distance, such as Manhattan distance (L1 norm), is computed between the query vector and all cluster centroids 170, which can be stored in the reference database 160. Based on the computed distances, a set of closest cluster centroids is identified for each of the query vectors. In one example, the set of closest cluster centroids includes twelve cluster centroids, which are at a least distance from a query vector are identified. Further, based on the set of closest cluster centroids identified for a query sequence, a corresponding query signature is generated.

At block 215, one or more target reference signatures (IRS) are identified, from a plurality of reference signatures for a given query sequence. For example, signature generation module 130 merges or concatenates the query signature with reference signatures 175 in the sorted data 150. Further, the merged query and reference signatures 175 are lexically sorted. The taxon assignment module 135 then identifies the target reference signatures from the sorted data 150. The sorted data 150 includes reference signatures 175 and query signatures in a sorted manner. The generation of reference signatures 175 corresponding to reference sequences 165 is explained in details with reference to description of FIG. 3.

In an implementation, the query signature is merged or concatenated with the reference signatures 175 in the sorted data 150. In an example, in case multiple query sequences are inputted, the corresponding query signatures of all the query sequences may be simultaneously merged with the reference signatures 175. Upon merging, the signatures in the sorted data 150 are sorted such that the sequences (query sequence and the reference sequences 165), which are phylogenetically similar are placed in proximity to each other. Once the signatures (query signature and reference signatures 175 are sorted, one or more target reference signatures for each query signature are identified. For example, a predetermined number of the reference signatures 175 lying on the either side of the query signature are identified as the target reference signatures.

At block 220, a value for a TA-flag is computed for each of the target reference signatures. The TA-flag represents a particular taxonomic level such that only taxa or clades of reference sequence lineage, which are either equal to or higher than the particular taxonomic level, are considered for binning the query sequence. In one implementation, to compute value for the TA-flags, a similarity score is computed for each of the target reference signatures. The taxon assignment module 135 then determines TA flags of target reference sequences based on respective similarity scores of the target reference sequences. The similarity score for a target reference signature is computed based on a positional match of cluster centroids 170 in the query signature and the target reference signature. Further, the cluster centroids 170 weightages in a target reference signature are progressively down weighted. The similarity score for an individual target reference signature is computed as the collective sum of the positional weightages obtained for all cluster centroid positions. The similarity score can be understood to be indicative of an extent of similarity between a target reference signature and the query signature. As mentioned before, based on the similarity score of the target reference sequence a value is computed for the TA-flag.

At block 225, it is determined if a proportion of the target reference signatures having the TA-flags corresponding to a given taxonomic level or a lower taxonomic level is less than a threshold TA-flag proportion. In one implementation, to initiate taxonomic assignment of the query sequence at the given taxonomic level, the taxon assignment module 135 determines the proportion of the target reference signatures that have TA-flags corresponding to the given or lower taxonomic levels. For example, the taxonomic classification may be initiated at genus level and accordingly the proportion of TA-flags corresponding to the genus level is computed and compared with the threshold TA-flag level. In another example, the taxonomic classification may be initiated at order level and accordingly the proportion of TA-flags corresponding to the order level, family level and genus level is computed and compared with the threshold TA-flag level.

If at block 225 it is determined that the proportion of the TA-flags corresponding to the given taxonomic level is in less than the threshold TA-flags proportion, block 225 branches to ("Yes" branch) block 230.

At block 230, it is determined if a next higher taxonomic level is root. For example, if at block 225 superkingdom level was selected and it is determined that for the superkingdom level, the proportion of the TA flags is less than the threshold TA flags proportion, then at block 230 it is determined if the next higher taxonomic level is root.

If at block 230 it is determined that the next higher taxonomic level is root, block 230 branches to ("Yes" branch) block 235. For example, if at block 225, the taxonomic level considered for taxonomic classification was superkingdom then at block 230 it may determined that the next higher taxonomic level is root.

At block 235, no taxon is assigned to query sequence and the query sequence is classified as "unassigned".

However, if at block 230 it is determined that the next higher taxonomic level is not root, block 230 branches to ("No" branch) block 225, where this higher taxonomic level is considered for determining the proportion of the TA-flags corresponding to the taxonomic level determined at block 230 and the lower taxonomic levels. For example, if at block 225, genus level was selected and the corresponding TA flags are at proportions less than threshold TA flag proportions, at block 230 it is determined that the next higher taxonomic level is family and not root, block 230 branches to ("No" branch) block 225, where the family level and genus level is considered for determining the proportion of the TA-flags.

If at block 225, it is determined that the proportion of the TA flags corresponding to the given taxonomic level or the lower taxonomic levels is greater than or equal to the threshold TA-flags proportion, block 225 branches to ("No" branch) block 240.

At block 240, a taxonomic level is identified based on a proportion of target reference signatures, i.e., based on a determination made at block 225. Accordingly, a taxon from the identified taxonomic level is selected for further analysis.

At block 245, a most common taxon belonging to the identified taxonomic level is selected. For the purpose, a taxon corresponding to each of the target reference signatures is determined and accordingly the taxon appearing a maximum number of times is selected as the most common taxon.

At block 250, it is determined if a proportion of the target reference signatures having the most common taxon is less than a threshold taxon proportion. If so, block 250 branches to ("Yes" branch) block 230, where it is determined that if a next higher taxonomic level is root. For example, if a taxon from order level is selected at block 245, then based on the analysis performed at block 250, at block 230 it is determined if a next higher level to order is root or not.

However, if at block 250, it is determined that the proportion of the target reference signatures having the most common taxon is greater than or equal to the threshold taxon proportion, block 250 branches to ("No" branch) block 255.

At block 255, the most common taxon is identified as a probable taxonomic group to which the query sequence may belong. Further, the probable taxonomic group is assigned to the query sequence.

In the present taxonomic classification technique analysis is performed with reference to signatures of the query sequences and the references sequences 165 instead of the sequences per se. The signatures are generated such that they are indicative of compositional similarity or to say phylogenetic similarity among reference and query sequences. Further, the signatures are sortable such that a single step of sorting can replace an exhaustive and computationally expensive All-vs-All sequence database search. This results in a substantial reduction in computational time and resources, ensuring reasonable levels of accuracy and specificity in parallel.

Referring to FIG. 3, the method 300 generates reference signatures for a plurality of reference sequences, according to an implementation of the present subject matter. The reference signatures 175 may be generated by a module, such as the signature generation module 130, of the taxonomic classification system 100.

At block 305, reference sequences may be retrieved and saved in a reference database, such as the reference database 160. In one implementation, the taxonomic classification system may communicate with an external database, such as Genbank, and retrieve the reference sequences 165 from the external database. The reference sequences 165 may be retrieved in the form of nucleic acid sequences. These nucleic acid sequences may include either coding sequences or non-coding sequences or sequences including both coding and non-coding regions from partially or completely sequenced genomes. Additionally or alternately, the reference sequences 165 may be retrieved in the form of amino acid sequences. Further, the reference database 160 may contain reference sequences 165 of either prokaryotic organisms or eukaryotic organisms or both.

At block 310, a reference vector corresponding to each of the reference sequences is generated. Reference vectors may be generated based on one or more compositional characteristics of the reference sequences 165. For example, the reference vectors may be generated based on frequencies of all possible tetra-nucleotides in the reference sequence 165 and the reference vectors may be represented in the form of 256 dimensional tetra-nucleotide frequency vectors.

At block 315, the reference sequences may be classified into reference clusters using a clustering technique, such as k-means clustering technique, based on the compositional characteristics of the reference vectors. In one implementation, the reference sequences 165 with similar oligonucleotide composition may be classified together in one cluster.

At block 320, a cluster centroid may be assigned to each of the reference clusters. The cluster centroid may be computed based on the reference sequences that lie in that cluster. A cluster centroid represents the mean value of the reference vectors corresponding to the reference sequences included in a particular reference cluster.

At block 325, for each of the reference sequences, a set of closest cluster centroids is identified. In one implementation, for each of the reference sequences 165, distances of the respective reference vector to all the cluster centroids 170 is computed. Based on the computed distances, a predetermined number of nearest cluster centroids to the reference vector are identified. The identified cluster centroids form the set of the closest cluster centroids.

At block 330, for each of the reference sequences, a reference signature is generated, based on the respective set of the closest cluster centroids. In one example, a reference signature 175 is generated by arranging the cluster centroids 170 identified at block 325 in an ascending order of their distances from a reference vector corresponding to the reference sequence 165 under consideration.

It will be understood that for generating a query signature corresponding to a query sequence, blocks 325 and 330 may be performed. The method 300 for generating reference signatures not only provides for reduction in the computational time and resources while implementing method 200, but also maintains accuracy and specificity of the present taxonomic classification technique comparable to the conventional taxonomic classification techniques.

Although embodiments for taxonomic classification have been described in language specific to structural features and/or methods, it is to be understood that the invention is not necessarily limited to the specific features or methods described. Rather, the specific features and methods are disclosed as exemplary embodiments for the taxonomic classification.

We claim:

1. A computerized method for assigning a probable taxonomic group to a query sequence comprising:
   creating the query sequence by sequencing genetic material obtained from an environmental sample;
   determining a query vector corresponding to the query sequence, based on a compositional characteristic of the query sequence;
   identifying a set of closest cluster centroids, based on a distance between the query vector and each of a plurality of cluster centroids, wherein each of the plurality of cluster centroids is associated with a reference cluster, the reference cluster including one or more reference sequences having similar compositional characteristic;
   generating a query signature corresponding to the query sequence based on a set of closest cluster centroids;
   sorting the query signature with respect to a plurality of reference signatures in a lexical order to position the query signature in a vicinity of compositionally similar reference signatures, each reference signature corresponding to a reference sequence;
   selecting, based on the sorting, one or more target reference signatures from the plurality of reference signatures, the one or more target reference signatures being the reference signatures similar to the query signature;
   identifying, based on the one or more target reference signatures, the probable taxonomic group, and
   assigning the probable taxonomic group to the query sequence.

2. The computerized method as claimed in claim 1, wherein the compositional characteristic includes one of an oligonucleotide frequency and a guanine-cytosine (GC) content.

3. The computerized method as claimed in claim 1, wherein the distances are one of Manhattan distances (L1 norm), Cosine measures, Chebyshev distances, Minkowski distances, and Mahalanobis distances.

4. The computerized method as claimed in claim 1, wherein the selecting comprises:
   merging the query signature with the plurality of reference signatures to sort the query signature; and
   determining one or more reference signatures that are similar to the query signature to provide the one or more target reference signatures.

5. The computerized method as claimed in claim 1, wherein the identifying comprises:
   computing a value of a taxonomic assignment flag (TA-flag) for each of the target reference signatures based on an extent of similarity between respective target reference signature and the query signature;
   determining a taxonomic level of the target reference signatures based in part on the values of the TA-flags; and
   selecting, as the probable taxonomic group, a most common taxonomic group associated with the one or more target reference signatures belonging to the determined taxonomic level, wherein the most common taxonomic group is a taxonomic group associated with a majority of the one or more target reference signatures.

6. The computerized method as claimed in claim 5, wherein determining the taxonomic level comprises:
computing a proportion of the target reference signatures having the values of the TA-flags corresponding to the taxonomic level and one or more underlying lower taxonomic levels; and
comparing the proportion of the TA-flags of the target reference signatures with a threshold TA-flags proportion.

7. The computerized method as claimed in claim 5, wherein the selecting as the probable taxonomic group comprises:
computing a proportion of the target reference signatures having the most common taxonomic group, when the proportion of the TA-flags of the target reference signatures is greater than the threshold TA-flags proportion; and
comparing the proportion of the target reference signatures having the most common taxonomic group with a threshold taxon proportion,
wherein the most common taxonomic group is identified as the probable taxonomic group, when the proportion of the target reference signatures having the most common taxonomic group is greater than the threshold taxon proportion.

8. The computerized method as claimed in claim 7, wherein selecting as the probable taxonomic group comprises:
determining whether a taxonomic level immediately higher to the determined taxonomic level is root, when one of a threshold TA-flags proportion criterion and a threshold most common taxonomic group proportion criterion is not met, the threshold TA-flags criterion being ascertaining whether the proportion of the TA-flags of the target reference signatures is greater than the threshold TA-flags proportion, and the threshold most common taxonomic group proportion criterion being ascertaining whether the proportion of the target reference signatures having the most common taxonomic group is greater than the threshold taxon proportion; and
binning the query sequences as 'unassigned' when the next higher taxonomic level is root.

9. The computer implemented method as claimed in claim 1, wherein the genetic material obtained from the environmental sample is sequenced using one of a Sanger sequencing technology and a 454 sequencing technology.

10. A taxonomic classification system comprising:
a processor; and
a memory coupled to the processor, the memory comprising:
a sequence creation module configured to create a query sequence by sequencing genetic material obtained from an environmental sample;
a signature generation module configured to:
determine a query vector corresponding to the query sequence, based on a compositional characteristic;
identify a set of closest cluster centroids, based on a distance between the query vector and a plurality of cluster centroids, wherein each of the plurality of cluster centroids is associated with a reference cluster, the reference cluster including one or more reference sequences having similar compositional characteristic; and
generate a query signature corresponding to a query sequence based on the set of closest cluster centroids; and
a taxon assignment module configured to:
sort the query signature with respect to a plurality of the reference signatures in a lexical order to place the query signature in the vicinity of compositionally similar reference signatures, each reference signature corresponding to a reference sequence;
select, based on the sorting, one or more target reference signatures from a plurality of reference signatures, the one or more tar et reference signatures being the reference signatures similar to the query signature;
determine a taxonomic level based in part on a value assigned to a taxonomic assignment flag (TA-flag) associated with each of the target reference signatures; and
identify a most common taxonomic group belonging to the determined taxonomic level, wherein the most common taxonomic group is assigned to the query sequence.

11. The taxonomic classification system as claimed in claim 10, wherein the signature generation module is configured to:
merge the query signature with the plurality of reference signatures to sort the query signature.

12. The taxonomic classification system as claimed in claim 10, wherein the signature generation module is further configured to:
generate a reference vector corresponding to each of a plurality of reference sequences, wherein the plurality of the reference sequences are classified into a plurality of reference clusters;
compute distances between each of reference vectors and the plurality of cluster centroids;
identify, for each of the reference vectors, a corresponding set of closest cluster centroids, wherein the corresponding set of closest cluster centroids is identified based on the respective computed distances; and
generate a reference signature for each of the reference vectors, based on their respective set of the closest cluster centroids.

13. The taxonomic classification system as claimed in claim 10, wherein the taxon assignment module is further configured to compute a similarity score for each of the target reference signatures to determine the value of the TA-flag assigned to respective target reference signatures, wherein the similarity score is indicative of an extent of similarity between the query signature and the target reference signatures.

14. The taxonomic classification system as claimed in claim 10, wherein one or more reference sequences are one of coding sequences, non-coding sequences, and sequences including a combination of coding and non-coding regions, wherein the reference sequences are derived from one of genome sequences and protein sequences.

15. The taxonomic classification system as claimed in claim 8, wherein the genetic material obtained from the environmental sample is sequenced using one of a Sanger sequencing technology and a 454 sequencing technology.

16. A non-transitory computer readable medium having computer executable instructions which when executed, implement a method comprising:
creating the query sequence by sequencing genetic material obtained from an environmental sample;

determining a query vector corresponding to the query sequence, based on a compositional characteristic of the query sequence;

identifying a set of closest cluster centroids, based on a distance between the query vector and each of a plurality of cluster centroids, wherein each of the plurality of cluster centroids is associated with a reference cluster, the reference cluster including one or more reference one or more reference sequences having similar compositional characteristic;

generating a query signature corresponding to a query sequence based on the set of closest cluster centroids;

sorting the query signature with respect to a plurality of reference signatures in a lexical order to position the query signature in the vicinity of compositionally similar reference signatures, each reference signature corresponding to a reference sequence;

selecting, based on the sorting, one or more target reference signatures from the plurality of reference signatures, the target reference signatures being the reference signatures similar to the query signature; and identifying, based on the one or more target reference signatures, a most common taxonomic group, wherein the most common taxonomic group is assigned to the query sequence.

17. The non-transitory computer readable medium as claimed in claim 16, wherein the identifying comprises:

computing a similarity score for each of the target reference signatures to determine the value of a TA-flag assigned to respective target reference signatures, wherein the similarity score is indicative of an extent of similarity between the query signature and the target reference signatures;

determining a taxonomic level of the target reference signatures based in part on the values of the TA-flags; and selecting, as a probable taxonomic group, the most common taxonomic group associated with the one or more target reference signatures belonging to the determined taxonomic level, wherein the most common taxonomic group is a taxonomic group associated with a majority of the one or more target reference signatures.

18. The non-transitory computer readable medium as claimed in claim 17, wherein determining the taxonomic level comprises:

computing a proportion of the target reference signatures having the values of the TA-flags corresponding to the taxonomic level and one or more underlying lower taxonomic levels; and comparing the proportion of the TA-flags of the target reference signatures with a threshold TA-flags proportion.

19. The non-transitory computer readable medium as claimed in claim 18, wherein the selecting as the probable taxonomic group comprises:

computing a proportion of the target reference signatures having the most common taxonomic group, when the proportion of the TA-flags of the target reference signatures is greater than the threshold TA-flags proportion; and comparing the proportion of the target reference signatures having the most common taxonomic group with a threshold taxon proportion.

20. The non-transitory computer readable medium as claimed in claim 19, wherein selecting as the probable taxonomic group comprises:

determining whether a taxonomic level immediately higher to the determined taxonomic level is root, when one of a threshold TA-flags proportion criterion and a threshold most common taxonomic group proportion criterion is not met, the threshold TA-flags criterion being ascertaining whether the proportion of the TA-flags of the target reference signatures is greater than the threshold TA-flags proportion, and the threshold most common taxonomic group proportion criterion being ascertaining whether the proportion of the target reference signatures having the most common taxonomic group is greater than the threshold taxon proportion; and binning the query sequences as 'unassigned' when the next higher taxonomic level is root.

21. The non-transitory computer readable medium as claimed in claim 17, wherein the genetic material obtained from the environmental sample is sequenced using one of a Sanger sequencing technology and a 454 sequencing technology.

* * * * *